(12) United States Patent
Goldsmith (10) Patent No.: US 7,591,837 B2
(45) Date of Patent: Sep. 22, 2009

(54) FACET TRIANGLE SPINAL FIXATION DEVICE AND METHOD OF USE

(75) Inventor: Michael E. Goldsmith, Potomac, MD (US)

(73) Assignee: Pyramid Spine, LLC, Ashburn, VA (US)

( * ) Notice: Subject to any disclaimer, the term of this patent is extended or adjusted under 35 U.S.C. 154(b) by 255 days.

(21) Appl. No.: 10/937,771

(22) Filed: Sep. 10, 2004

(65) Prior Publication Data

US 2005/0119657 A1 Jun. 2, 2005

Related U.S. Application Data

(60) Provisional application No. 60/514,744, filed on Oct. 28, 2003.

(51) Int. Cl.
*A61B 17/70* (2006.01)
(52) U.S. Cl. .................. 606/247; 606/246; 606/279
(58) Field of Classification Search .............. 606/61, 606/69–71; 623/17.11–17.16; 248/65, 226.11, 248/534
See application file for complete search history.

(56) References Cited

U.S. PATENT DOCUMENTS

| | | | |
|---|---|---|---|
| 600,421 A * | 3/1898 | Holcombe | 248/539 |
| 5,403,316 A | 4/1995 | Ashman | |
| 5,415,661 A * | 5/1995 | Holmes | 606/69 |
| 5,498,263 A * | 3/1996 | DiNello et al. | 606/61 |
| 5,607,425 A | 3/1997 | Rogozinski | |
| 5,643,261 A | 7/1997 | Schafer et al. | |
| 5,928,232 A | 7/1999 | Howland et al. | |
| 6,022,350 A * | 2/2000 | Ganem | 606/61 |
| 6,102,954 A | 8/2000 | Albrektsson et al. | |
| 6,123,706 A | 9/2000 | Lange | |
| 6,146,382 A | 11/2000 | Hurlbert | |
| 6,347,904 B1 * | 2/2002 | Knighton | 403/400 |
| 6,454,769 B2 | 9/2002 | Wagner et al. | |
| 6,565,605 B2 * | 5/2003 | Goble et al. | 623/17.11 |
| 6,592,578 B2 * | 7/2003 | Henniges et al. | 606/27 |
| 2001/0037111 A1 | 11/2001 | Dixon et al. | |
| 2002/0045898 A1 | 4/2002 | Freid et al. | |
| 2002/0143329 A1 * | 10/2002 | Serhan et al. | 606/61 |
| 2003/0050640 A1 | 3/2003 | Lee et al. | |
| 2003/0153915 A1 | 8/2003 | Nekozuka et al. | |

(Continued)

FOREIGN PATENT DOCUMENTS

FR 2714591 * 7/1995

(Continued)

OTHER PUBLICATIONS

Deguchi et al., "Biomechanical Evaluation of Translaminar Facet Joint Fixation", Spine, 23(12):1307-1312 (1998).

(Continued)

*Primary Examiner*—Eduardo C Robert
*Assistant Examiner*—David Comstock
(74) *Attorney, Agent, or Firm*—Perry E. Van Over & Associates, PLLC (57) ABSTRACT

A device and method enables surgeon to bilaterally secure two vertebrae together in a stable and strong manner. A kit includes the device and ancillary instrumentation to facilitate the method of the present invention.

20 Claims, 11 Drawing Sheets

U.S. PATENT DOCUMENTS

2003/0191470 A1* 10/2003 Ritland .................. 606/61
2005/0033434 A1* 2/2005 Berry .................. 623/17.14

FOREIGN PATENT DOCUMENTS

FR         2786684      *    6/2000

OTHER PUBLICATIONS

Heggeness et al., "Translaminar Facet Joint Screw Fixation For Lumbar and Lumbosacral Fusion, A Clinical and Biomechanical Study", Spine, 16:S266-269 (1991).

Humke et al., "Translaminar Screw Fixation of the Lumbar and Lumbosacral Spine, A 5-Year Follow-Up", Spine, 23(10):1180-1184 (1998).

Lu et al., "Translaminar Facet Screw Placement: An Anatomic Study", Am. J. Orthop., 27(8):550-555 (1998).

Margulies et al., "Clinical Efficacy of Lumbar and Lumbosacral Fusion Using the Boucher Facet Screw Fixation Technique", Bull Hosp. Jt. Dis., 59(1):33-39 (2000).

PCT International Search Report, Form PCT/ISA/210 mailed Oct. 6, 2005.

* cited by examiner

FACET TRIANGLE SPINAL FIXATION DEVICE AND METHOD OF USE

This application claims priority from U.S. Provisional Application Ser. No. 60/514,744 filed Oct. 28, 2003. The entirety of that provisional application is incorporated herein by reference.

BACKGROUND OF THE INVENTION

1. Field of the Invention

The present invention relates to a novel spinal fixation device. More particularly the present invention relates to a novel one-piece device configured to bilaterally secure two vertebrae together in a manner that increases the stability and strength of the connection between the vertebrae. Also provided is a spinal fixation system by which a first spinal fixation device according to the present invention can be secured to a second spinal fixation device in such a manner so as to provide for two or more sequentially aligned vertebra to be securely attached one to the other. A method of securing two or more vertebrae one to the other is also disclosed.

2. Background of the Technology

The biomechanics and strength of facet screws and translaminar facet screws have been studied extensively. In addition, numerous clinical studies of these devices have also been reported. Facet screws have been used in a very limited manner for spinal fixation in the United States. Facet screws and translaminar facet screws have seen limited use in spine surgery, being primarily applied as an adjuvant to anterior interbody grafts. When employed in this fashion they serve as a posterior tension band by locking the facet joint. Facet screws are therefore extremely straightforward in application. However, the concern with their use is the limited fixation and rigidity that they are able to provide. To improve on this deficiency, translaminar facet screws have been advocated. Further, the use of translaminar facet screws provided improved strength through purchase into the cortical aspect of the lamina and the spinous process prior to entering the facet joint. However, the risk for dural laceration and nerve injury increases dramatically when this device is used as compared to the use of a regular facet screw. In addition, the angle of application is such that a longer or separate incision must be made far lateral and a trocar must be placed in a blind fashion through significant spinal musculature. For these reasons, the surgical application of the translaminar facet screw can be very challenging.

Alternatively, the use of pedicle screws has been demonstrated to be a very rigid and reliable means of spinal fixation. In fact, it is possible that many pedicle screw spinal fixation systems are too rigid and, as a result, stress shield the fusion area. Moreover, the application of pedicle screws in spinal fixation can have many potential pitfalls. Since the pedicle cannot be directly visualized, multiple methods have been developed to locate the pedicle and apply the screw in the appropriate location, with the proper angulation, and the correct superior/inferior trajectory. Use of anatomic landmarks is helpful in making such application, but it is by no means perfect. Even the most skilled surgeons can be misled by aberrant anatomy. Even in straightforward anatomical situations, pedicles can have various diameters and significant variations in trajectory exist within the normal bell curve of the population. For these reasons, imaging is used by many surgeons to facilitate the surgical application of pedicle screws. Various intra-operative imaging modalities exist including fluoroscopy, flouroscan, and CT-image guidance. The former imparts significant radiation to the surgical team while the latter two incur significant cost and increased operating room time. All three modalities increase surgical time, potentially increase infection rate, and incur cost.

Furthermore, the surgical application of screws takes significant time. In addition, when screws are applied prior to decortication of the lateral gutters and application of bone graft, the screws often decrease the visualization of the gutters necessary for proper preparation. Further, the upper numbered screw many times has to be placed extremely close to, if not through, a facet joint that is not involved in fusion. This additional intrusion may, in the future, result in pain secondary to facet irritation. As an example of such additional and unwanted intrusion, in an L4-L5 fusion procedure, the L4 screw is placed at the level of the L3-4 facet joint. Finally, inappropriate or inaccurate pedicle screw placement can lead to disastrous consequences. For example, if a screw is misplaced, the resulting breakout of the pedicle can incur nerve root irritation, dural laceration, and spinal cord injury if above the L1-L2 region, and disc space disruption, and potential vascular damage if placed too far anterior.

Because of the great concern over misplaced pedicle screws, intraoperative imaging is necessarily used as stated above. In addition, for safety reasons neurological monitoring of somatosensory evoked potentials and EMG stimulation of the screws are used by many surgeons. The imaging and monitoring incur significant additional costs for the surgical procedure.

A need therefore exists for a spinal fixation device and method that provides improvements over conventional devices in the attachment of two vertebra to each other with reduced risk to the patient, less surgical time, cost and trouble to apply and dependably strong security of attachment.

In an attempt to decrease the risk and cost associated with the application of pedicle screws, an alternative form of fixation over that conventionally used has been devised: the facet triangle device. The device of the present invention is a simple concept that is easy, quick, safe, and cost-effective to use. Further, the facet triangle device provides a rigid construct in one, two, and more level lumbar fusions.

SUMMARY OF THE INVENTION

The facet triangle and method of application of the present invention provides a novel one-piece device and method to enable a surgeon to bilaterally secure two vertebrae together in a manner that increases the stability and strength of the connection over that previously known in the art.

Also provided is a one-piece device that can be easily constructed so as to be quickly and accurately fitted to the many variations in size and shape of the particular subject's vertebra to which the device is to be attached.

Also provided is a one-piece device for securing two vertebra together such that the device can be quickly and safely surgically applied to the vertebra of a subject without the need for conventionally required intraoperative imaging.

Also provided is a kit that includes at least one of the novel devices of the present invention, a set of securing members or screws adapted for fixing the device to the bone of a subject, surgical instruments configured to be capable of facilitating the insertion of the device into a subject and the fixation of the device to a bone of the subject.

Also provided is a method of applying the novel device of the present invention such that the surgical procedure, in comparison to conventional methods, is quickly accomplished with low risk to the subject to which the device is being surgically attached.

DETAILED DESCRIPTION OF THE INVENTION

The present invention provides a novel one-piece device, which can be viewed as a facet triangle, and a method to enable a surgeon to use that device to bilaterally secure two vertebrae together in a manner that increases the stability and strength of the connection. The present invention provides a quick, safe, and effective method of fixing two vertebra together in a way that provides numerous other benefits over conventional fixation devices and methods.

The present invention, as compared to the commonly used pedicle screws has a minimal risk of nerve impingement secondary to being able to apply the device under direct visualization. The present invention requires less operative time for the subject thus decreasing blood loss experienced in longer surgical procedures. The incision required to accomplish the present invention is minimal when using a tension band in conjunction with anterior lumbar interbody fusion (ALIF). Further, unlike conventional procedures, the method of the present invention has no need for fluoroscopy or other imaging systems during the course of the surgery. Similarly, with the present invention there is no need for EMG monitoring or Somatic Sensory Evoked Potential (SSEP) monitoring, which are commonly required for such procedures. Ultimately, there is decreased cost (for one level fusion, use two screws and one device whereas with pedicle screws, a surgeon would need four screws and two rods). Further, the cost of EMG, flouroscopy, and increased operating room time normally experienced with pedicle screw procedures can be saved.

The present invention as compared to the use of translaminar facet screws realizes cost savings in that there are no separate far lateral incisions needed and no risk of penetration of lamina with the possibility of dural or nerve root injury. Further, the result of the present invention is a more rigid fixation secondary to linkage of two screws locked to the device. Also, unlike translaminar facet screw techniques, the present invention does not rely upon intact lamina therefore may be done in conjunction with complete laminectomy. Finally, as compared to the use of facet screws alone, the present invention can provide a much more rigid, linked system but still be manufactured to have similar rigidity to pedicle screws with interconnecting rods.

In addition to all of the advantages of the present invention recited above, the present invention provides a device, a method, and a kit that can be used by a surgeon to fix two or more vertebra in a much more secure manner that heretofore was possible. The present invention as shown in FIGS. 1-10X and as discussed in the accompanying description is limited only by the claims attached hereto.

As shown in FIGS. 1-10X, the facet triangle device (10) includes an elongated member (12) having a first planar-surface (14) and a second planar surface (16). The elongated member includes a first end (18) and a second end (20). Between the first end (18) and second end (20), is provided a central portion (22). The central portion (22) is formed to have a generally inverted V-shaped configuration such that said first planar surface (16) is angled inward toward itself and away from the longitudinal axis of the elongated member (12).

Both the first end (18) and the second end (20) include a terminal portion (24) (26), the terminal portions being bent inward toward the first planar surface (14) and away from the longitudinal axis of the elongated member (12) so as to form an angle between the terminal portions (24) (26) and the central portion (22) respectively adjacent to the each terminal portion (24) (26). The terminal portions (24) (26) provide a foot plate at each end of the device (10) that serve as attachment points to the vertebra.

Figure 9A:
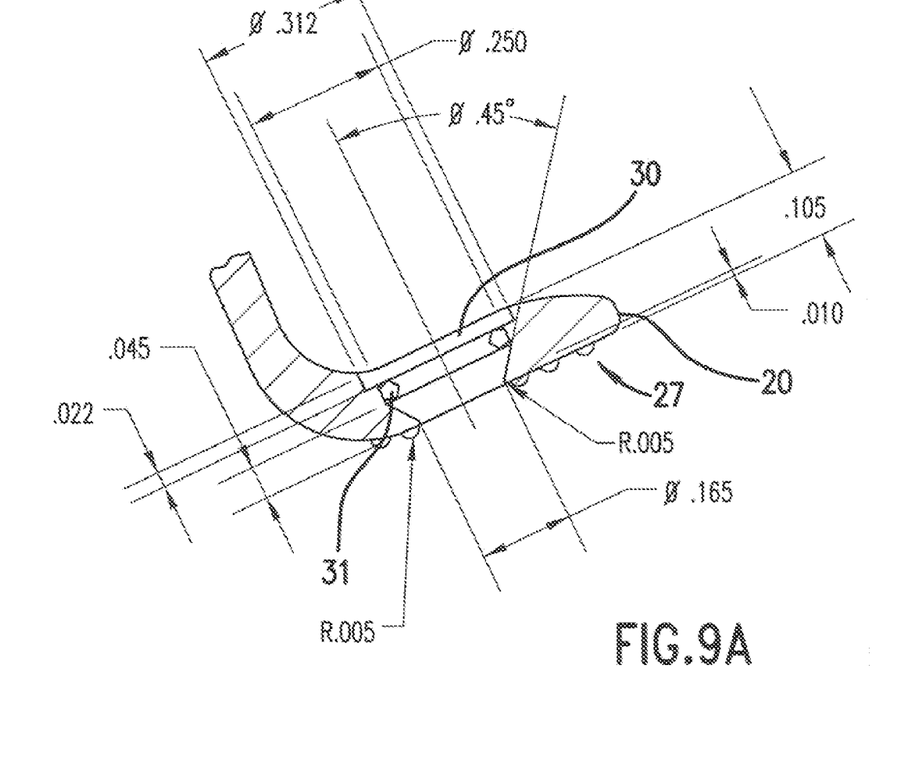
FIGS. 9A-9B show one embodiment of a device according to the present invention with a non-limiting example of the conformation and dimensions of one of the securing portals of the device.
Figure 9B:
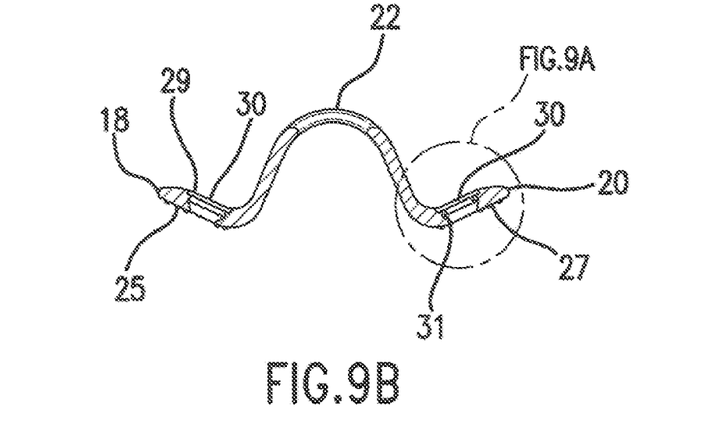

As best shown in FIGS. 9A and 9B, the underside of the terminal portions (24, 26) or volar surface of the foot plates (25, 27) of the device in the vicinity of the securing portals (28, 30) can be textured to improve the contact with the bone and thereby reduce motion. This texturing can be accomplished by any way known in the art to texture a surface, to include, for example rough grit blasting, machine textured, or providing with a porous coating. It is also within the scope of the present invention for the volar aspect of the foot plates (25, 27) to be smooth, knurled, crosshatched, or provided with tines for griping the bone. Preferably, the foot plates (25, 27) will be textured in some manner so as to improve friction and device-to-bone contact. Preferably, the ends of the elongated member (12) will be contoured, for example to have a bullet-end conformation to allow ease of dissection in minimally-open surgical insertion procedures.

Figures 8A, 8B, 8C, 8D, 8E:
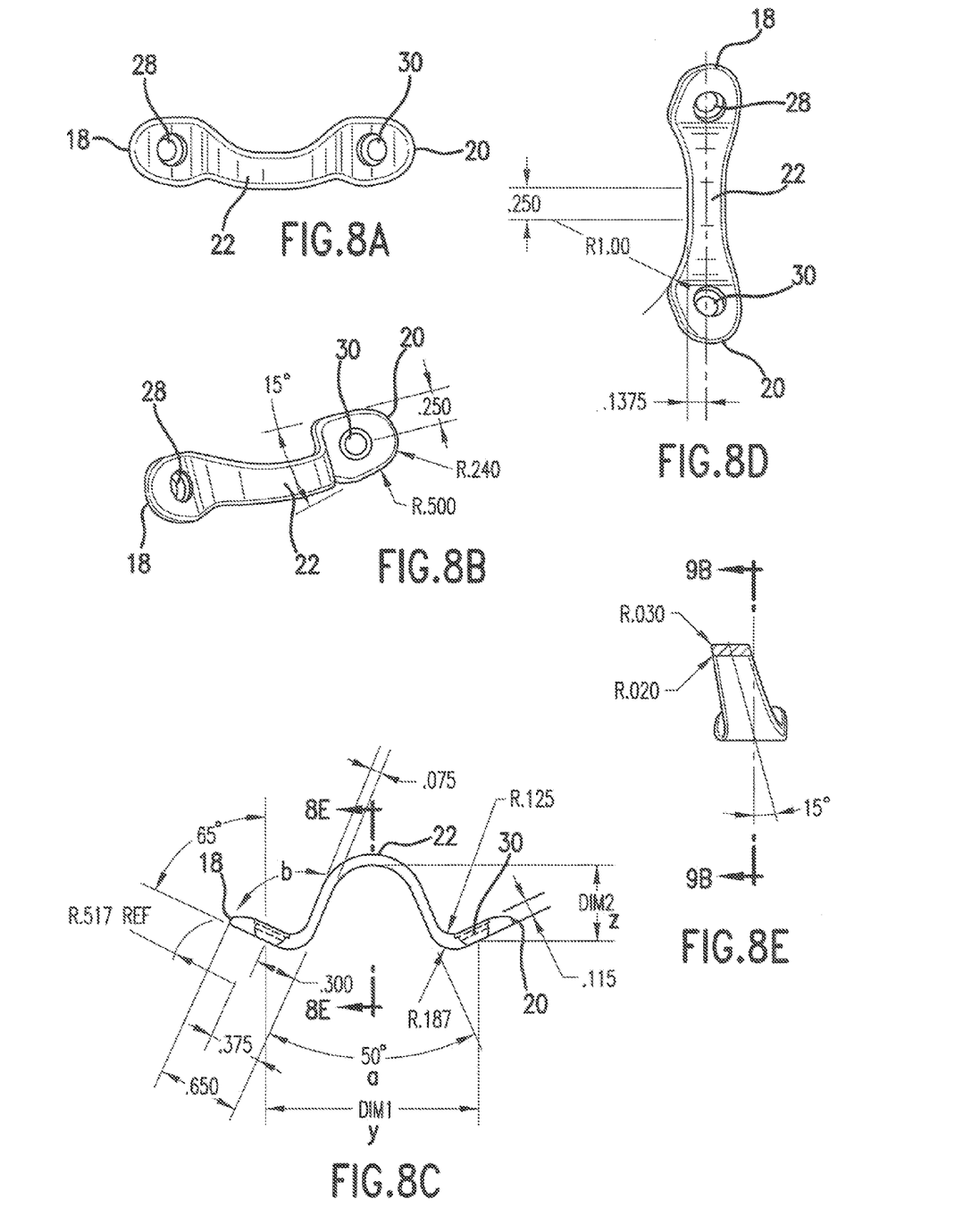
FIGS. 8A-8E show different perspective views of the present invention with non-limiting examples of the conformational variety and the relative dimensions and angles that can be employed in the manufacture of the device so as to provide a configuration for the device that is well-adapted to fit the unique shape and size for a particular vertebra to which the device is to be attached.
Figure 10A:
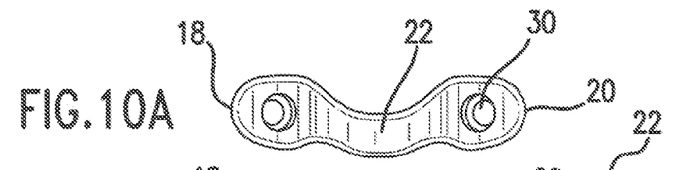
FIGS. 10A-10X show depictions of a series of top, front, and side elevations of embodiments of the present invention, which vary in size and conformation as necessary to accurately fit to the subject's vertebra.
Figure 10B:
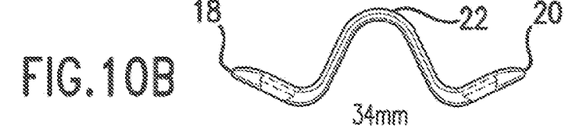
Figure 10C:
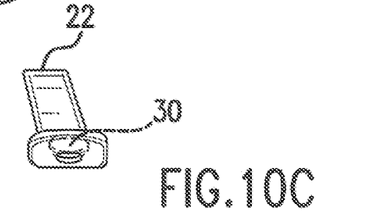
Figure 10D:
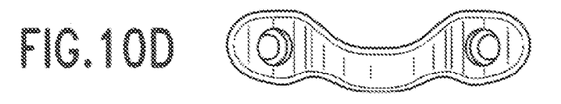
Figure 10E:
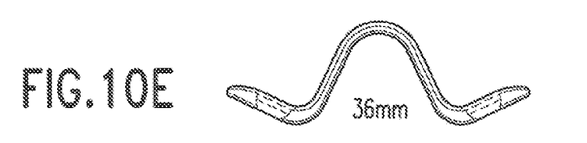
Figure 10F:
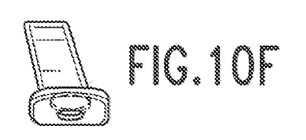
Figure 10G:
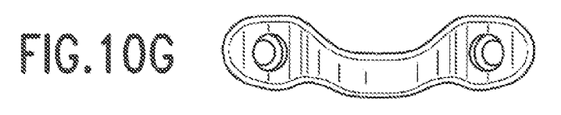
Figure 10H:
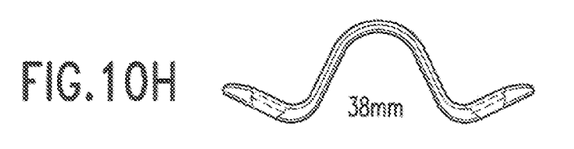
Figure 10I:
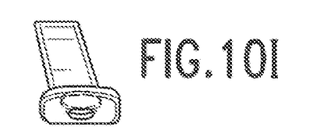
Figure 10J:
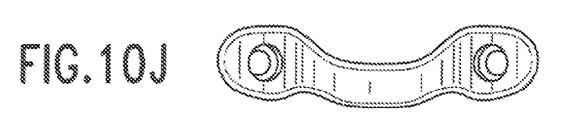
Figure 10K:
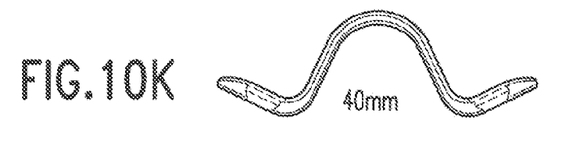
Figure 10L:
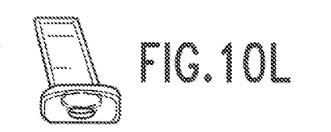
Figure 10M:
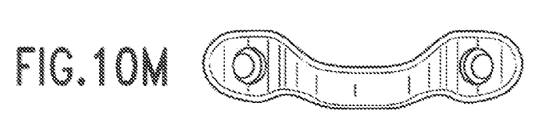
Figure 10N:
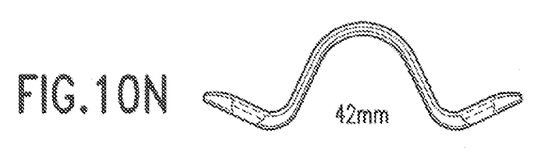
Figure 10O:
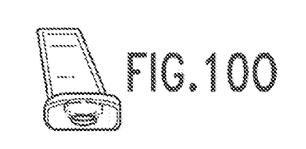
Figure 10P:
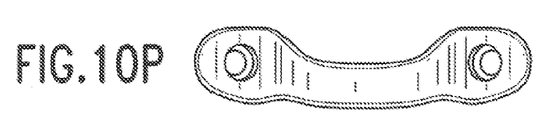
Figure 10Q:
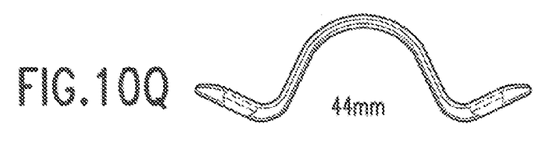
Figure 10R:
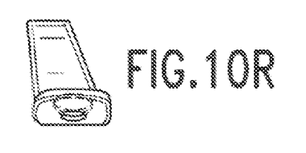
Figure 10S:
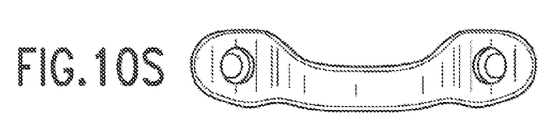
Figure 10T:
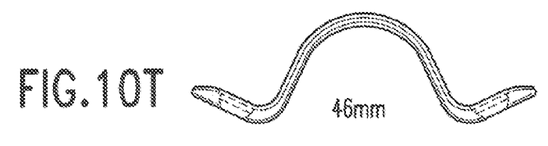
Figure 10U:
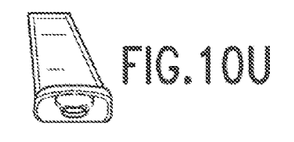
Figure 10V:
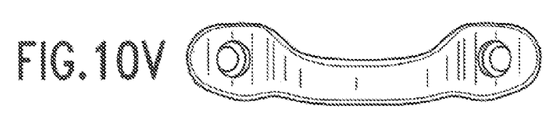
Figure 10W:
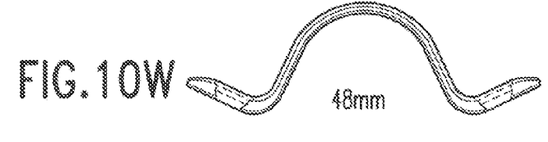
Figure 10X:
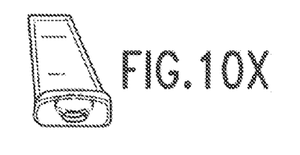

Importantly, the device will include a twist angle (c), which is formed by the axis of the foot plate and the longitudinal axis of the central portion (22) of the device. Due to the twist angle (c), the terminal portions (28, 30) will be angled caudal and lateral such that the foot plates will be angled downward toward the coccyx and outward. The degree of angulation is best shown in FIG. 8E. The degree of angulation in the conformation of the device of the present invention can be varied as necessary so as to provide the best fit possible of the device to the unique configuration of the vertebra of the subject to which the device is to be attached. As best shown in FIG. 10A-10X, the variation of device configuration is well demonstrated in a comparative presentation of non-limiting examples of different conformations of the device (10) as determined by the distance between the two securing portals (28, 30). Importantly, the conformation of the device can be varied as necessary so as to select the best fit embodiment of the device to complement the specific configuration of the vertebra of interest.

Figure 5:
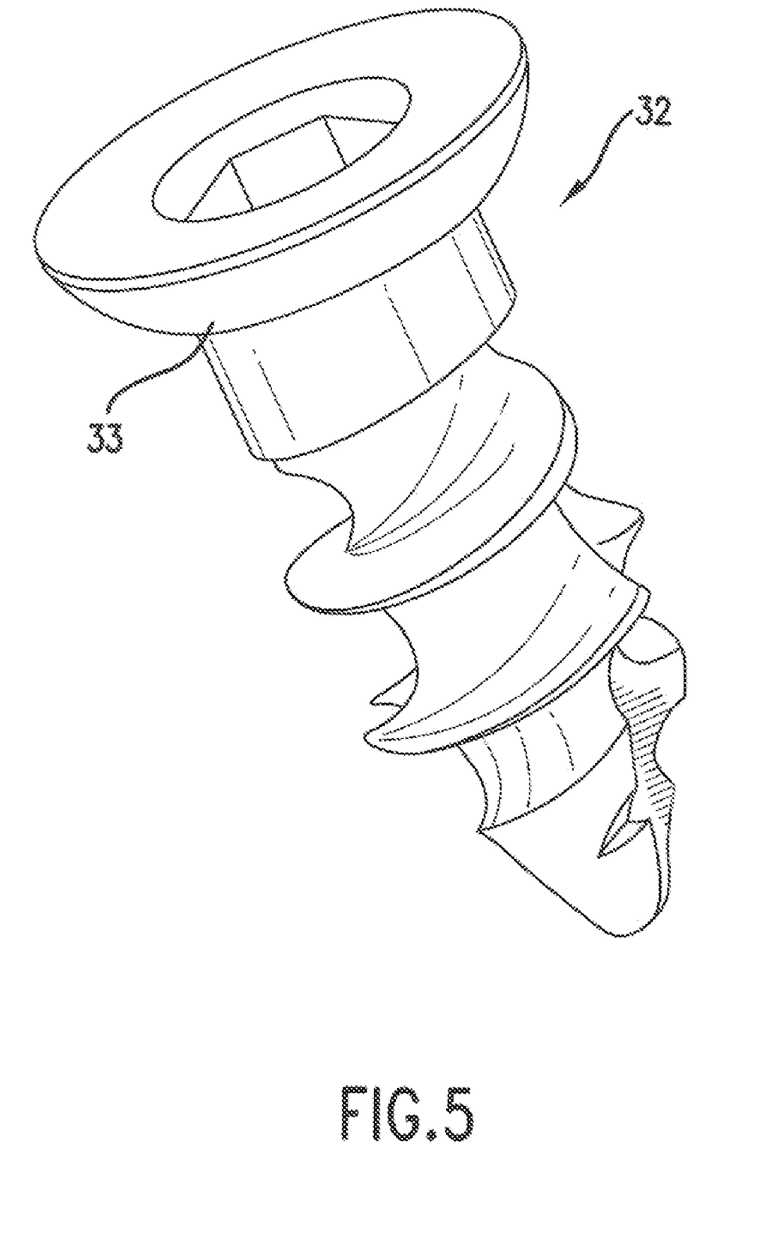
FIG. 5 shows a detail of a non-limiting example of a facet screw that is suitable for use with the device of the present invention.

Each of the terminal portions defines a securing portal (28) (30) that passes there through. The securing portals (28) (30) are sized and configured to accept a securing member (32) (preferably a self-tapping screw), which is configured to secure the device (10) to the spinal column, generally shown at (34), and more precisely to secure the device to the facets (36) (38) of a vertebra (40). A non-limiting example of a securing member (32) is shown in FIG. 5. Any securing member (32) known in the art that could be adapted to secure the device (10) of the present invention to the bone of a subject can be employed without departing from the concept of the present invention. Non-limiting examples of securing members (32) that are acceptably used with the present invention include, fully threaded cortical screws, partially threaded cortical screws, cancellous fully threaded screws, and partially threaded cancellous screws. Typically, the diameter of the securing members used in the present invention will be between 3.5-4.5 mm but may be of any size or shape without departing from the concept of the present invention. The securing members (32), like the device (10) can be manufactured of any strong material that is surgically acceptable such as titanium alloy or stainless steel.

Finally, to facilitate entry of the device (10) into the body of a subject undergoing such a surgical procedure, the contours of the device can be specifically formed to ease such physical insertion. Furthermore, the edges of the terminal portions (28, 30) can be smoothly tapered so as to facilitate insertion of the device through a small external incision in the subject.

The degree of bend in the elongated member (12) to form the inverted V-shaped configuration is individually determined by the distance between the facets (36) of each vertebra (40) to which it is secured. The securing members (32) can be lockably engaged with the elongated member (12). This can be accomplished simply by having complementary threads in the securing members (32) and the securing portals (28, 30). Other locking mechanisms that can be employed within the concept of the invention include for example, cam locks, which screw to the device, inclusion of a metal strip in the device, which is employed from the top and slides distally to cover screw holes, a retaining ring (31) seated in the securing portals (28, 30) that captures the securing member (screw), and a screw within the securing member (32) that expands the head of the securing member (32) into the securing portal (28, 30). Securing members (32) having a rounded portion below the head of the member can be employed as complementary to the securing portals (23, 30) such that a tight secure fit can be obtained between the two even though the securing member (32) can be angled within the securing portals (28-30). Such flexibility in positioning the securing member (32) allows the user to direct the securing member (32) into the bone of a subject at the optimum angle to ensure a secure fixation of the device to the bone. The angle of the axis of the securing member (32) to the axis of the securing portals (28, 30) can easily vary from 0 to 10 degrees or more, so long as a secure connection to the vertebra is obtained. Larger angles, such as, for example about 30 degrees, are within the concept of the invention, however, it is extremely unlikely that such a higher angle would be necessary to obtain a secure connection between the device and the bone to which it is affixed. As best shown in FIGS. 9A-9B, the securing portals (28, 30) can be provided with a spherical countersink (29) that is complementary in conformation to the curvature of the underside (33) of the head of the securing member (32).

Figure 6:
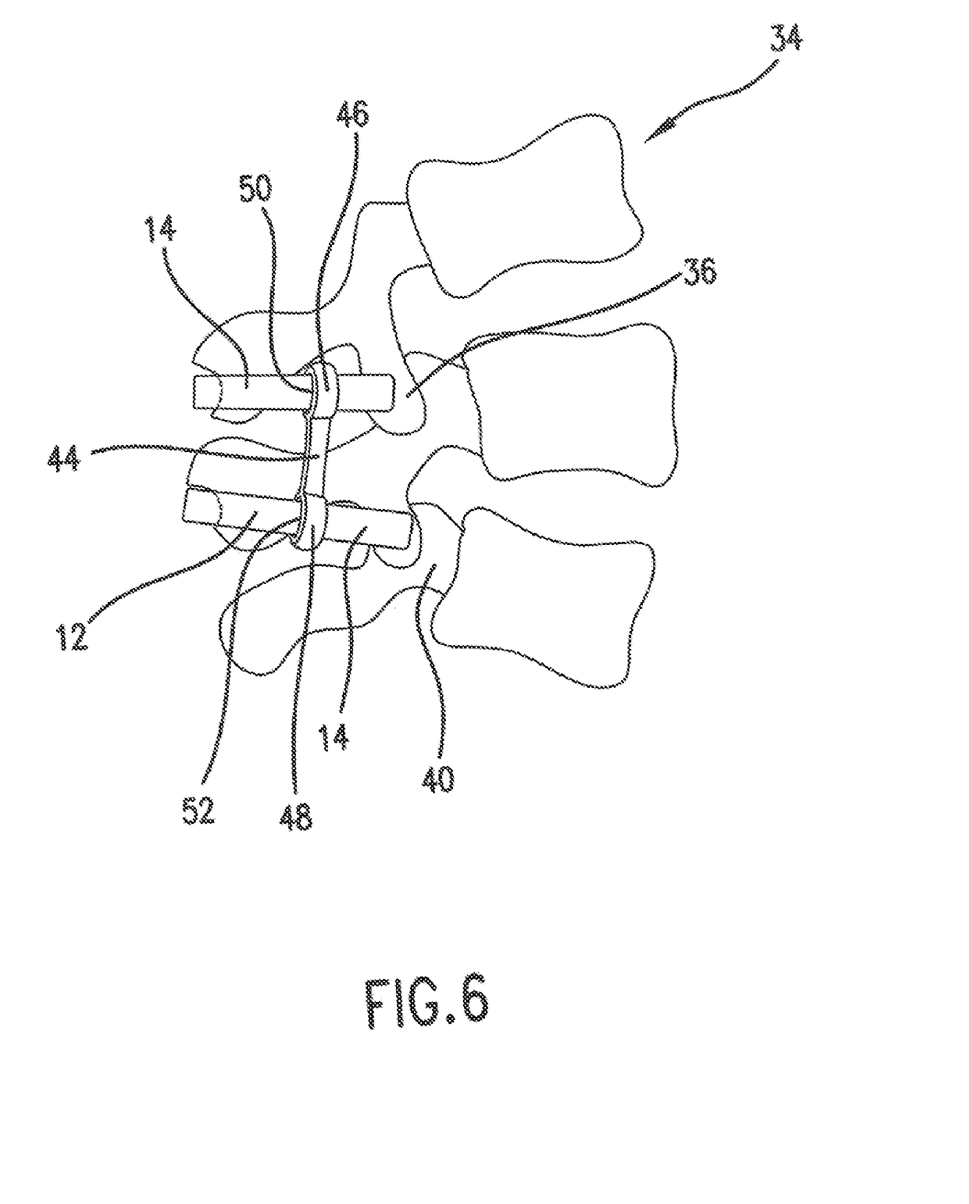
FIG. 6 shows a lateral view of an example of multiple devices attached to sequential vertebrae and connected one to another within the concept of the present invention.
Figure 7:
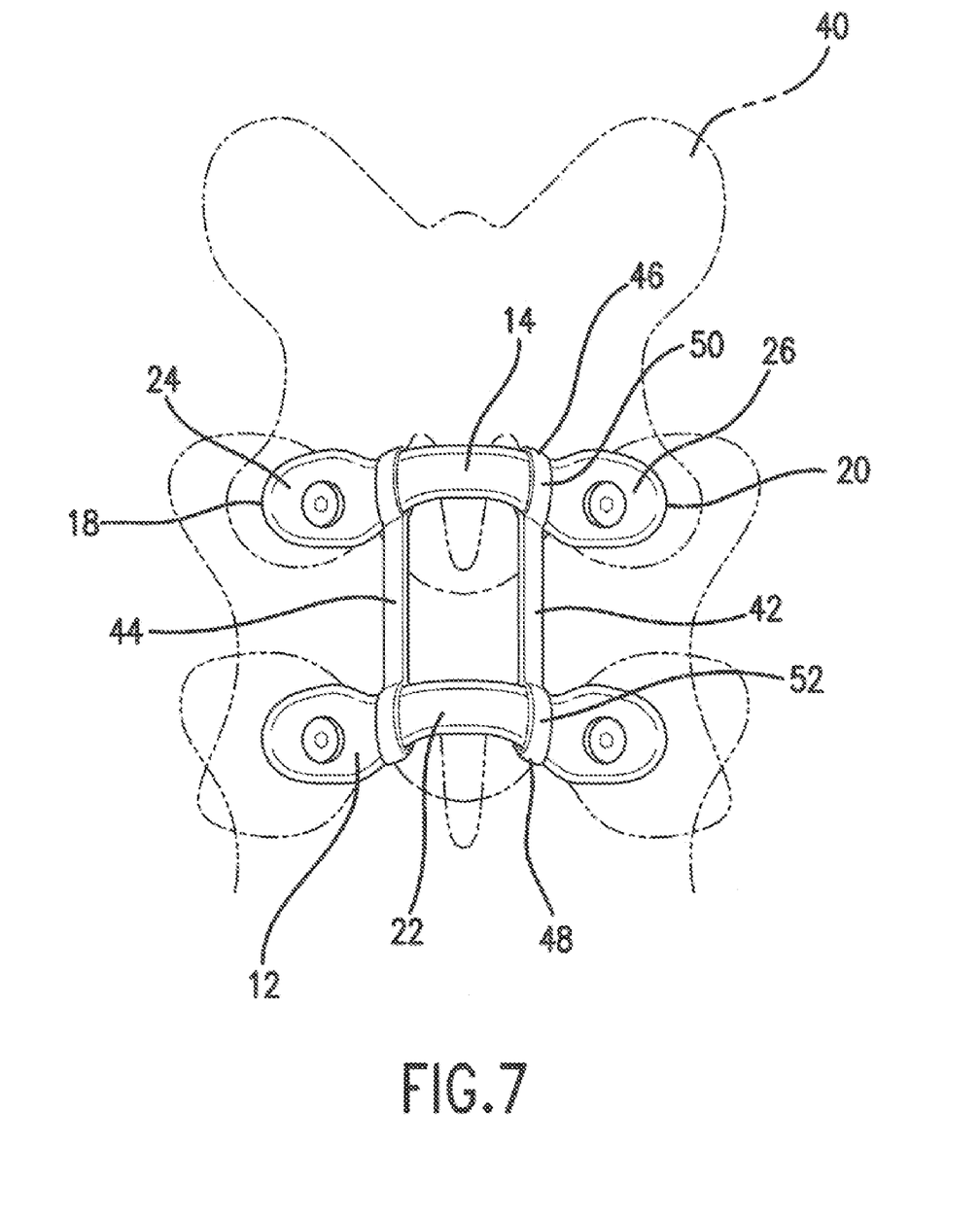
FIG. 7 shows a posterior diagrammatic presentation of the embodiment of the present invention shown in FIG. 6.

As shown in FIG. 6 (a lateral perspective of three vertebra) and FIG. 7 (a diagrammatic, top view of vertebra shown in dashed lines), more than one Facet Triangle (10) can be attached to a respective number of adjacently aligned vertebra (40) and secured in relation to each other by parallel elongated in-line connection members (42) (44), each having a connector first end (46) and a connector second end (48). The in-line connection members (42) (44) can be configured to have a connector portal (50) (52) located proximate to each of the connector first end (46) and the connector second end (48). The connector portals (50) (52), when secured circumferentially around the device (10) are sized and configured to be large enough to permit passage of the elongated member 12 through the portal but small enough to provide secure attachment of the Facet Triangle (10) to the connection members (42) (44). The connection members (42) (44) can be any mechanical, releasably attached member as is known in the art. They can be fixed in length or adjustable as is also known in the art.

In practice, the device can be used by a surgeon to meet the requirements of spinal fixation in response to many conditions. The following non-limiting examples of abnormal conditions of the vertebral column are well-suited for treatment by a surgeon applying the device and method of the present intention. The device can be used in a subject suffering from degenerative spondylolisthesis for one or more vertebral levels after complete or incomplete laminectomy as necessary. Another vertebral column malady for which the present device could be used in treatment is degenerative disc disease wherein a posterior tension band to augment an anterior interbody fusion is applied. Use of the device is also indicated in the treatment of degenerative disc disease after 1-level posterior lumbar interbody fusion or trans-foraminal lumbar interbody fusion (TLIF); for TLIF facet screw on contralateral side and fixation into the transverse process on ipsilateral side. The present invention is also well suited for use in degenerative disc disease: after two-level or three-level TLIF, involving securing of the ipsilateral plates with a unilateral construct. The process of the invention is also well suited in cases where multiple recurrent Herniated Nucleus Pulposes (HNP) indicated that fusion is needed to prevent recurrence.

More specifically, in cases of Iatrogenic instability, if pars is removed, a straight plate needs to be used ipsilaterally into the remaining facet. Proximally, purchase is made into superior articular facet of upper numbered vertebrae in fusion. The facet joint above must be preserved by purchasing only the superior articular facet and leaving alone the inferior articular facet of the vertebrae above. For example, for a L4-5 fusion, a straight plate is used bilaterally. The inferior screw purchases the remaining L4-5 facet joint; the superior screw is inserted into the L4 superior articular facet and the L3 inferior articular facet is not purchased. In this fashion, the L3-4 facet joint is actually preserved.

The following is an abbreviated non-limiting exemplary description of a surgical procedure employing the device and method of use of the present invention.

Pre-surgery evaluation of the subject and particularly of the size, position, and configuration of the vertebra to which the device is to be attached determines what size range and conformation range of the device will be best suited to provide a complementary fit of the device to the subject's vertebra. The pre-surgery survey of the subject permits the provision of a device (10) in sizes and conformations that bracket the expected need for the device in surgery.

The method of the present invention can involve surgically exposing the dorsal surface of the spinal column of a subject sufficiently to permit attachment of the device (10). Upon exposure of the dorsal surface of the vertebra, precise measurement and conformational evaluation is done to determine what size device having what configuration will be best suited to the needs of the subject. The device (10) to be used is then selected for application to the subjects vertebra. The pre-surgical device group selection process and the post vertebra exposure device final selection process is possible due to the precise manufacturing and forming of the device so as to permit a best-fit selection without unnecessary delays at the time of surgery. Ideally, the device to be applied to the subject's vertebra will be initially provided to the user in the form of a kit, which includes a group or range of different sizes and configurations of the device, one or more of which may be used for the subject during the surgery. The group of devices that can be provided in such a kit can be preselected for size and configuration during the pre-surgery evaluation by the surgeon. The at least one device (10), which is ultimately selected for attachment to the vertebra will be sized, configured, and contoured to facilitate attachment and ensure the best fit of the device to the contours of the bone to which it is secured.

When only one vertebral level is involved, the following non-limiting exemplary surgical process would be typical for a skilled practitioner using the device of the present invention.

The 3.5 cortical screws/4.5 cortical screws are angled into the facet joint through the respective securing portal (28, 30). Holes to receive the cortical screws can be pre-drilled into the bone with a 2.5 mm/3.2 mm drill. Length can be measure with a standard depth gauge as is known in the art. The depth may or may not include fixation into the base of the transverse process or sacrum based on the surgeon's preference. The screws are preferably self-tapping screws. When securely in place, the screws (32) can lock to the securing portal (28, 30) of the elongated member (12). This can be done, for example, by threadably engaging the screws (32) with the securing portals (28, 30) or by inclusion of a retaining ring (31) in the securing portals (28, 30) of the device (10).

Figure 1:
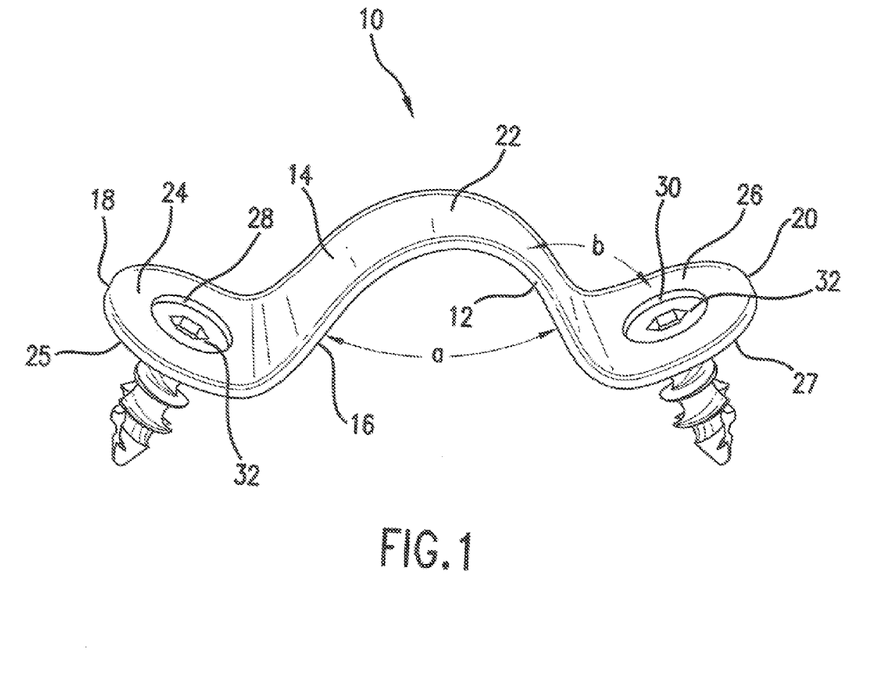
FIG. 1 shows a frontal perspective view of the device of the present invention.
Figure 2:
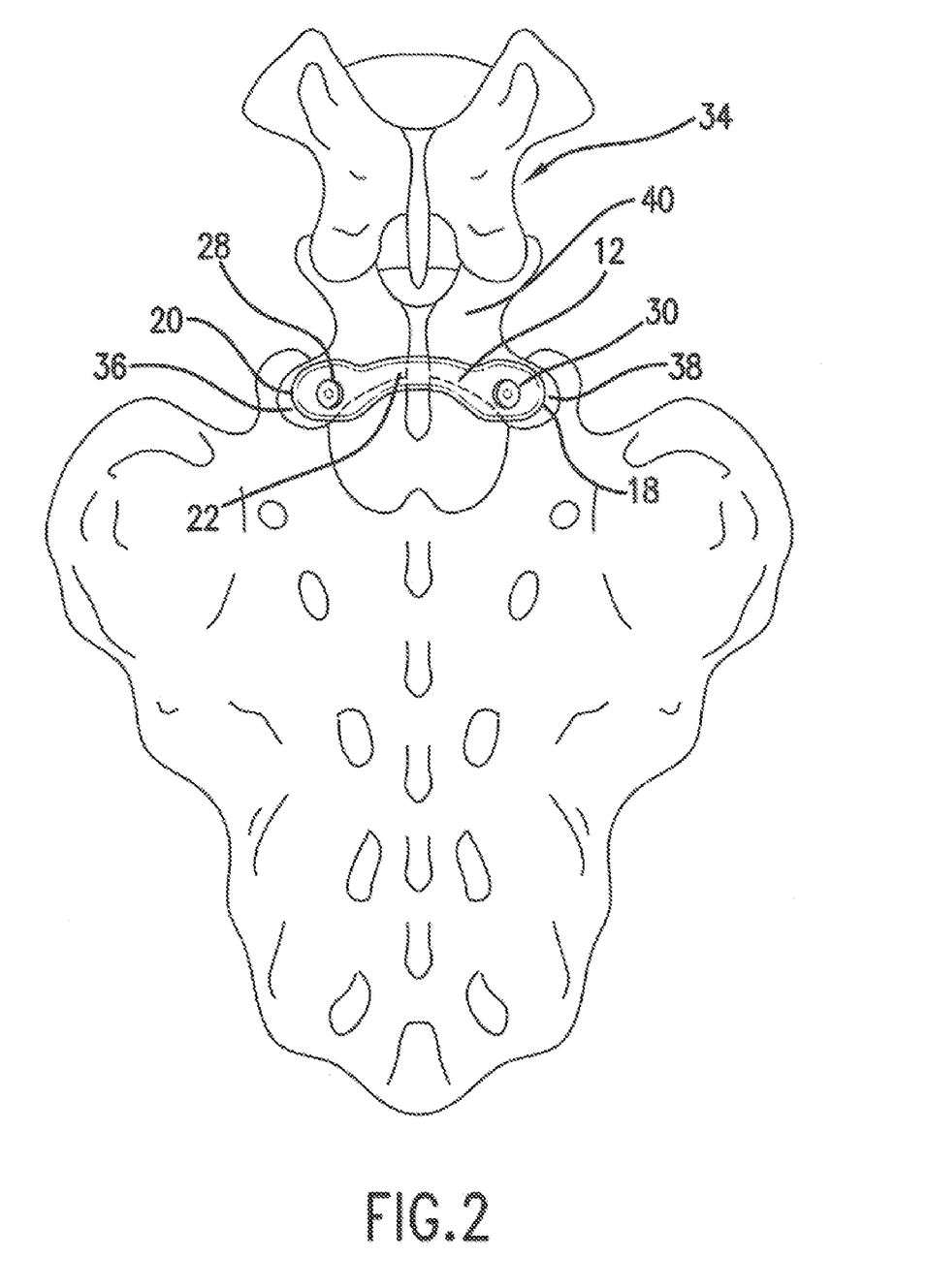
FIG. 2 shows a top view of an example application of the device of the present invention used to attach L5 to S1 in a subject as seen from the posterior view of the vertebral column.
Figure 3:
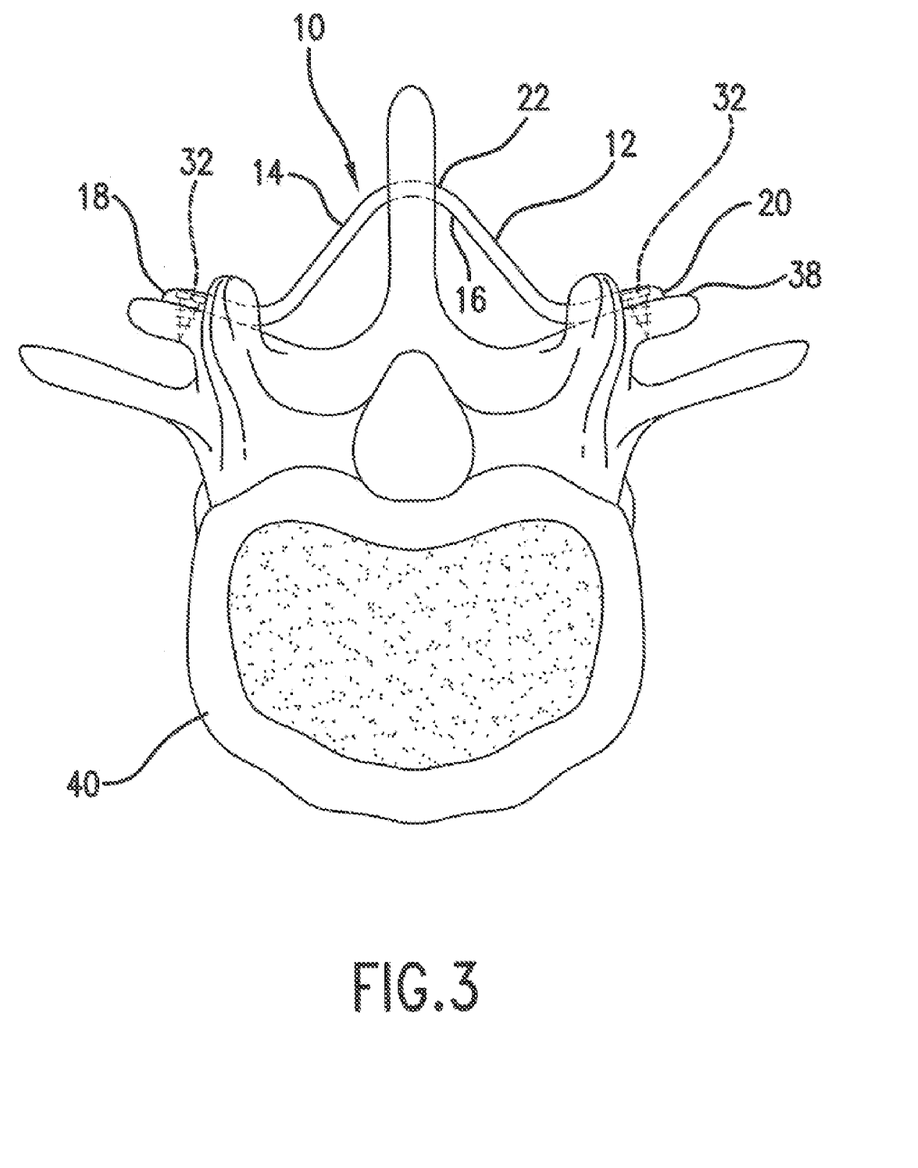
FIG. 3 shows a front view of the device of FIG. 1 as it would be applied to the vertebra of a subject, the view perspective is a caudal aspect of the vertebra; that is being along the longitudinal axis of the vertebra column.
Figure 4:
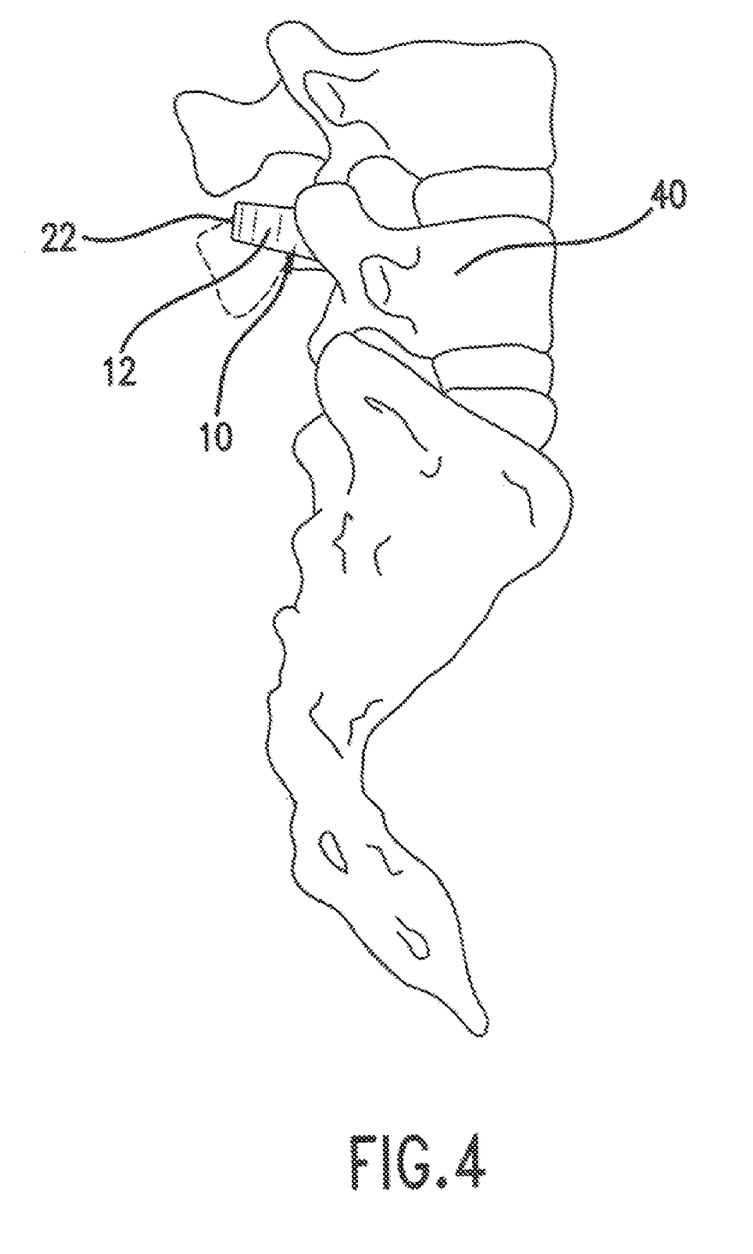
FIG. 4 shows a lateral view of an example application of the device of the present invention used to attach L4 to L5 in a subject as seen from the lateral view of the vertebral column.

If a laminectomy has not been performed, some spinous process and possible dorsal lamina may need to be removed to allow proper contouring of the device (10) to the spine. FIGS. 2, 3, and 4, respectively provide a posterior, caudal, and lateral view of the device (10) appropriately placed and attached to the vertebra. The lateral view provides an indication of the contouring or notching of the spinous process that may be necessary. Preferably the spinous process of the vertebra will be notched as shown in dashed lines in FIG. 4 so as to allow the angle of the "V" of the Facet Triangle to lie within the notch for a smooth contour.

For surgical procedures involving two or more levels, a device (10) is employed for each level. Each of the devices (10) are secured to the respective vertebra as described above. The two or more devices (10) may be connected one to another by the in-line connection members (42) (44) described above.

Examples of the Device

An important aspect of the present invention is the provision of a preselected group of individually sized and configured devices (10) that are manufactured based upon the teaching of the present invention so as to provide a best possible fit to the vertebra of the subject in need of surgical treatment.

Multiple sizes and configurations of the facet triangle device (10) are manufactured based initially upon the width between the facet joints as evaluated by the user during pre-surgery evaluations and finally at the time of exposure of the vertebra during surgery. The distance between the facets can be measured with a caliper and then tested in-situ. A non-limiting example of the invention would be to provide such typical widths as from 25 mm-55 mm in 5 mm increments (7 sizes) with three different angles of the screws for each size (30, 45, and 60 degrees). The lower down in the lumbar spine, the less the angle may be required. In such a non-limiting example, screw lengths can vary from 25-60 in 2 mm increments. The device (10) can be manufactured to have a wide variety of widths and configurations based on the experiential analysis of various vertebra conformations. Minor conformational corrections to the conformation of the finally selected device (10) can be accomplished by bending the center of the device (10) if adjustment is needed within the 5 mm increments of the different-sized devices (10).

For ipsilateral fixation, the devices (10) are comparatively straight, having a lessened angle in the inverted V-shape configuration. For procedures involving two vertebral levels, devices (10) can be sized between 20-45 mm in 5 mm increments (6 sizes). Each size device (10) can be manufactured to have various options at each securing portal (28, 30). To ensure security, the device can be provided with more than the exemplary two securing portals (28, 30). For example, for devices (10) having three holes, the gap between holes is staggered and the angles varied as necessary to ensure a best-fit to the bone to which it will be secured. The concept of the present invention allows for the possibility of cross-connectors between the straight, ipsilateral plates.

As discussed above, the concept of the invention that permits providing a device (10) that is sized and configured to very closely complement the size and conformation of the vertebra to which it is to be attached is a major benefit over the one size fits all approach of many conventional spinal fixation devices. The one-piece construction of the Facet Triangle provides a simple, strong, easily used spinal fixation device that is far superior to any conventional device or attachment. In addition to it's obvious benefits, the manufacture and provision of a kit that includes a select group of such devices (10) that have first been preselected and then finally selected to give a best-fit of the device (10) to the subject's vertebra is an important aspect of the invention that results in the strongest possible connection of the device (10) to the subject's vertebra.

As best shown in FIGS. 10A-10X, the dimensions, angles, and configuration of the device (10) can be varied considerably to provide a best fit to the vertebra of the subject undergoing the surgical procedure. As best shown in FIG. 1, FIG. 8A-8E, and FIG. 9A-9B, a non-limiting example of the device (10) is provided with exemplary, specific physical dimensions and angles. In this non-limiting example, the length (y) of the device is taken from center of securing portal (28) to center of securing portal (30) and typically measures at 45 mm±1 cm. The height of the device (z)=17 mm±5 mm. In this non-limiting example, the center angle (a), that the two arms of the device (10) subtend, is 60 degrees, with the top of the device (10) contoured or rounded to form an inverted V-shape.

A central portion angle, (b), subtended between each of the foot plates (25, 27) and the respective arm of the inverted V shape, can be 60-180 degrees, preferably is between 60-140 degrees 120-125 degrees, and more preferably between 80-130 degrees. This angle (b) can be varied as necessary to achieve good conformation to the vertebra to which it will be attached.

The twist angle (c) (coronal angulation) that the foot plate (25, 27) makes with longitudinal axis of central portion (22) of the device (10), the inverted V, provides a torsional twist or caudal angulation that can be about 15 degrees. This twist angle (c), as best shown in FIG. 8E, is intended to facilitate the security of screw entry through the device and into the underlying bone material. The twist angle (c) can be varied from 0-60 degrees depending upon the specific dictates of the configuration of the bone to which the device (10) will be attached.

The width (x) of elongated member (12) of the device (10), in this example, can be about 7 mm. The width (x) can be varied as necessary to fit the configuration of the subject's vertebra, for example, to be 5-15 mm wide or more.

In general, the width (x) of device can flair out or widen to provide a larger foot print of the foot plates (25, 27) of the device (10) on the surface of the bone. Such a widening of the foot plates (15, 27) can provide sufficient surrounding structure to define the securing portals (28, 30) without sacrificing strength. The foot plates (25, 27) can be 5 to 15 mm wide but preferably are approximately 10-15 mm wide and more preferably are 12-14 mm wide.

While a fixed angle (a) formed in a substantially rigid device (10) is preferred, it is within the concept of the invention to provide a "bend zone" at or proximate to the inverted V-shaped portion (22) of the device (10) with a malleable nature to allow for fine adjustments of the device configuration or to provide a hinged-center of the device so that a variable angle in the one device can be obtained. Importantly, the bend zone of the device (10) would be formed such that the surgeon could manipulate and select the desired configuration at the time of the surgery and then secure the selected angle by use of a hinged portion as the "bend zone" or by use of a locking screw, securing catch, or reinforcing member that could be used once the desired angle was set.

Similarly, while it is preferred that the angle between foot plates (25, 27) and the inverted V portion (22) of the elongated member (12) base of plate is fixed and manufactured based on the inventions concept of providing a wide range of device sizes and configurations designed to conform to the size and shape of the vertebra at issue, it is still within the scope of the invention to provide a hinged angle or a malleable bend zone with or without a locking mechanism for the foot plate (25, 27) angle. In such an embodiment, once a set screw is secured into the device, the hinge would lock automatically. Alternatively, the device could be equipped with a locking mechanism separately employed in the hinge itself, i.e., a set screw to lock the device.

Further to the more general description of sizes and configurations of an exemplary device provided above, the device (10) depicted in FIGS. 8A-8E shows the device as it would be depicted for a specific size and angle conformation. The angles and sizes, while presented very specifically, are still only representative of a device that can be manufactured in a wide range of sizes and configurations. The Examples of FIG. 8A-8E are expanded by viewing them with the aid of the dimensions of other representative devices that can be manufactured based on the same principles of the present invention. See Table 1.

TABLE 1

| Example Device | Dimension 1 | Dimension 2 | Size (mm) |
| --- | --- | --- | --- |
| A | 1.339 | .500 | 34 |
| B | 1.417 | .520 | 36 |
| C | 1.496 | .540 | 38 |
| D | 1.575 | .560 | 40 |
| E | 1.654 | .580 | 42 |
| F | 1.732 | .600 | 44 |
| G | 1.811 | .620 | 46 |
| H | 1.811 | .640 | 48 |

Each of the embodiments described above are provided for illustrative purposes only and it is within the concept of the present invention to include modifications and varying configurations without departing from the scope of the invention that is limited only by the claims included herewith.

What is claimed is:

1. A device for the fixation of two vertebra of a subject one to the other, the device comprising:
    an elongated member having a longitudinal axis, said elongated member terminating at a first end of said longitudinal axis in a first terminal portion and terminating at a second end of said longitudinal axis at a second terminal portion;
    a first securing portal defined within and passing through said first terminal portion and a second securing portal defined within and passing through said second terminal portion; said elongated member being sized and configured to extend transversely across a first vertebra of a subject such that when said device is in use and fitted in said transverse relationship to said vertebra, said first securing portal will be positioned over a first facet of said first vertebra and said second securing portal will be positioned over a second facet of said vertebra;
    a central portion of said elongated member connecting said first terminal portion to said second terminal portion; said central portion being upwardly displaced from said longitudinal axis so as to form an upward curvature in the central portion of said elongated member, said central portion also being displaced laterally to form a twist angle;
    a first and a second securing member, each having a head portion and an elongated bone penetration portion, said bone penetration portions being sized and configured to respectively pass through said first securing portal and said second securing portal and having sufficient length to also pass through a portion of bone of an adjacent first vertebra and a portion of bone of an underlying second vertebra such that when in use, said first and second securing members serve to secure the device at both the first end and the second end of said elongated member to said first vertebra and said second underlying vertebra such that said first and second vertebra are secured one to the other and at least one connection member configured to rigidly and immovably fix said first vertebra to said second vertebra.

2. The device according to claim 1, wherein said elongated member is of unitary construction.

3. The device according to claim 1, wherein said twist angle is between 0-60 degrees.

4. The device according to claim 1, wherein said first terminal portion and said second terminal portion respectively form a first foot plate and a second foot plate, said first foot plate and said second foot plate each being formed so to be displaced away from the longitudinal axis of the elongated member in the same direction as the central portion is displaced from the longitudinal axis, said terminal portion displacement forming a foot plate angle of the device.

5. The device according to claim 4, wherein said foot plates have a wider dimension than said central portion of said device.

6. The device according to claim 1, wherein said first and second terminal portions of said elongated member have a larger width dimension relative to the width dimension of the central portion of the elongated member.

7. The device according to claim 1, wherein each of said first foot plate and said second foot plate have an under surface, said under surface of said first foot plate and said second foot plate being configured to be adjacent to the attachment surface of the vertebra and being textured to improve device to bone contact and attachment security.

8. The device according to claim 7, wherein said first and second securing portals are each configured to have a spherical countersink that is complimentary in shape to said head portion of each of said securing members so as to facilitate angling of the securing member within the securing portal such that, when in use, the securing member can have a variable secure member entry angle into the underlying vertebral bone material.

9. The device according to claim 8, wherein said entry angle of the securing member can be varied up to 30 degrees without changing the position of the foot plate against the underlying vertebra.

10. The device of claim 7, wherein the underside of said foot plates have a surface of a type selected from the group consisting of smooth, grit-blasted, machine-textured, porous-coated, knurled, crosshatched, and provided with tines.

11. The device according to claim 1, wherein said securing members are selected from the group consisting of common screws; self-tapping screws, fully threaded cortical screws, partially threaded cortical screws, cancellous fully threaded screws, and partially threaded cancellous screws.

12. The device according to claim 1, wherein said underside of said foot plates comprise splines to facilitate good contact with the underlying bone surface.

13. The device according to claim 1, further comprising a pair of retaining rings, each one of said pair of retaining rings being positioned radially around the inner circumference of a respective securing portal, said retaining ring serving to exert a retaining force on said securing member that is fully seated within the respective securing portal.

14. The device of claim 1, wherein said central portion and said foot plate form an upwardly directed central portion angle, said central portion angle being between 60 and 140 degrees.

15. A kit for use in a surgical procedure to fuse at least two adjacent vertebrae, one to the other, the kit comprising: at least one device according to claim 1, associated tools for said device, and a sterile package for said kit.

16. The kit according to claim 15, wherein said at least one device is a plurality of said devices of varying size and configuration.

17. A method of treating a subject in need of treatment requiring fusion of at least one vertebra to another, the method comprising:

pre-surgical evaluation of vertebra conformation of said subject;
providing at least one device for fixation of two vertebra, said device comprising:
an elongated member having a longitudinal axis, said elongated member terminating at a first end of said longitudinal axis in a first terminal portion and terminating at a second end of said longitudinal axis at a second terminal portion;
a first securing portal defined within and passing through said first terminal portion and a second securing portal defined within and passing through said second terminal portion; said elongated member being sized and configured to extend transversely across a first vertebra of a subject such that when said device is in use and fitted in said transverse relationship to said vertebra, said first securing portal will be positioned over a first facet of said first vertebra and said second securing portal will be positioned over a second facet of said vertebra;
a central portion of said elongated member connecting said first terminal portion to said second terminal portion; said central portion being upwardly displaced from said longitudinal axis so as to form an upward curvature in the central portion of said elongated member, said central portion also being displaced laterally to form a twist angle;
providing a first and a second securing member, each having a head portion and an elongated bone penetration portion, said bone penetration portions being sized and configured to respectively pass through said first securing portal and said second securing portal of said device and having sufficient length to also pass through a portion of bone of an adjacent first vertebra and a portion of bone of an underlying second vertebra surgically exposing at least a portion of the dorsal aspect of said at least one vertebra;
using said first and second securing members to pass through said first and second securing portals to attach said device to said first vertebra and to immovably fix said first vertebra to said second underlying vertebra.

18. A method of treating a subject in need of treatment requiring fusion of two or more vertebra to portions of corresponding underlying vertebra, the method comprising:
following the method of claim 17 for each of said two or more vertebra;
connecting the devices used for each of the two or more vertebra one to the other such that the respective device for each vertebra is fixed in position to the device of an adjacent vertebra.

19. The method of claim 18, wherein said connecting step is accomplished by use of at least one in-line connection member, a first end of said connection member being attached to a first device attached to a first vertebra and a second end of said connection member being attached to a second device attached to an adjacent vertebra.

20. The method of claim 19, wherein said at least one in-line connector is two connectors each positioned in an approximate parallel relationship one to the other, each being located on opposite sides of the spinal processes of the so connected adjacent vertebra.

* * * * *